(12) United States Patent
Weinberg

(10) Patent No.: US 6,207,111 B1
(45) Date of Patent: Mar. 27, 2001

(54) SYSTEM FOR DESCRIBING THE PHYSICAL DISTRIBUTION OF AN AGENT IN A PATIENT

(75) Inventor: Irving N. Weinberg, Bethesda, MD (US)

(73) Assignee: PEM Technologies, Inc., Bethesda, MD (US)

(*) Notice: Subject to any disclaimer, the term of this patent is extended or adjusted under 35 U.S.C. 154(b) by 0 days.

(21) Appl. No.: 09/002,048

(22) Filed: Dec. 31, 1997

(51) Int. Cl.[7] .............................. G01N 23/00; A61B 6/00
(52) U.S. Cl. ..................... 422/82.05; 422/71; 436/64; 436/57; 600/407; 600/431; 600/436
(58) Field of Search .................... 422/71, 82.05; 436/64, 57; 378/62, 37; 600/407, 411, 414, 420, 426, 427, 431, 436

(56) References Cited

U.S. PATENT DOCUMENTS

| | | | |
|---|---|---|---|
| 4,837,795 | * | 6/1989 | Garrigus . |
| 4,932,412 | * | 6/1990 | Goldenberg . |
| 4,960,709 | * | 10/1990 | Silvestrini . |
| 5,094,835 | * | 3/1992 | Kassis et al. . |
| 5,252,830 | * | 10/1993 | Weinberg . |
| 5,323,006 | * | 6/1994 | Thompson et al. . |
| 5,383,472 | * | 1/1995 | Devlin et al. . |
| 5,520,182 | * | 5/1996 | Leighton et al. . |
| 5,694,933 | * | 12/1997 | Madden et al. . |
| 5,813,985 | * | 9/1998 | Carroll . |
| 5,871,013 | * | 2/1999 | Wainer et al. . |

\* cited by examiner

Primary Examiner—Deborah Jones
Assistant Examiner—Jennifer McNeil
(74) Attorney, Agent, or Firm—Welsh & Katz, Ltd.

(57) ABSTRACT

A system for describing the physical distribution of an agent that accumulates selectively in tissue of a patient in an excised surgical specimen. The system comprises an agent which selectively concentrates in a cancer or precancer or focus of infection or other pathological condition. The system comprises a detector sensitive to the agent which is present in the surgical specimen. The system also comprises an apparatus capable of forming an image based on the information gathered by the detector, and which image describes the physical distribution of the agent in the surgical specimen so that a surgeon can be guided by the image provided by the apparatus, said apparatus connected to said detector.

10 Claims, 5 Drawing Sheets

RESECTED SPECIMEN CONTAINING CANCER INVISIBLE TO EYE, SLICED BY PATHOLOGIST

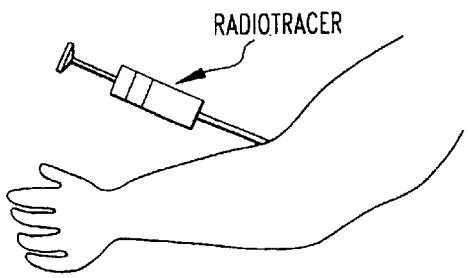

A. PRESURGICAL ADMINISTRATION OF RADIOTRACER THAT SELECTIVELY ACCUMULATES IN CANCER

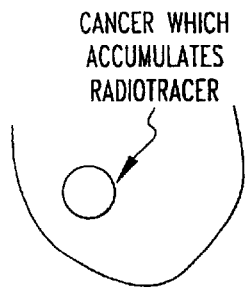

B. ACCUMULATION OF RADIOTRACER IN BODY PART PRIOR TO SURGERY

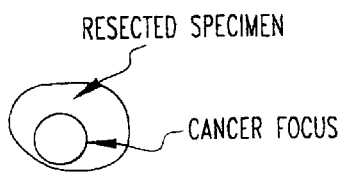

C. RESECTED SPECIMEN CONTAINING CANCER INVISIBLE TO EYE

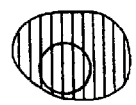

D. RESECTED SPECIMEN CONTAINING CANCER INVISIBLE TO EYE, SLICED BY PATHOLOGIST

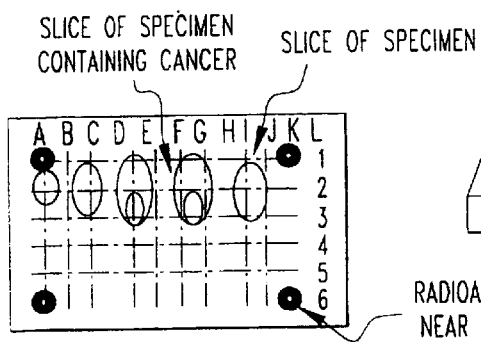

E. SLICED SPECIMEN ARRANGED IN ORDER BY PATHOLOGIST ON GRIDDED TRAY CONTAINING LEAD MARKERS AND RADIOACTIVE MARKERS

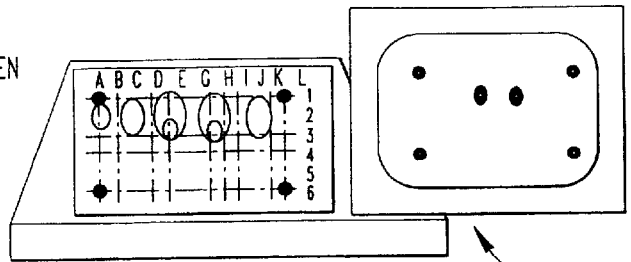

F. CAMERA SENSITIVE TO BETA RAYS OF RADIOTRACER COLLECTS AND DISPLAYS IMAGES OF RADIOACTIVITY ACCUMULATED IN SLICED SPECIMEN, AND OF RADIOACTIVE MARKERS

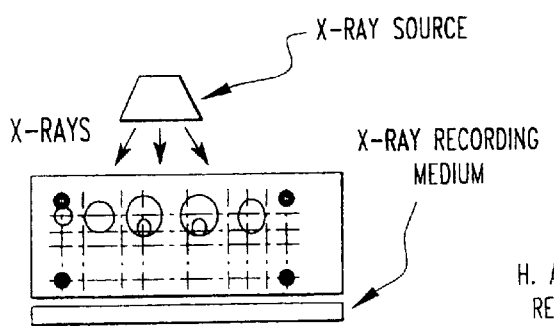

G. X-RAY CAMERA TAKES X-RAY ATTENUATION IMAGES OF SLICED SPECIMEN FOR COMPARISON

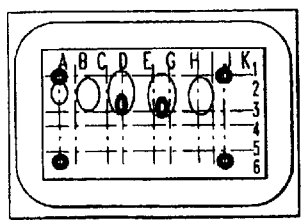

H. APPARATUS DIGITIZES X-RAY ATTENNUATION IMAGE, REGISTERS X-RAY IMAGE TO BETA RAY IMAGE, AND DISPLAYS BETA RAY IMAGE OVERLAID ON X-RAY IMAGE.

FIG.1

SYSTEM FOR DESCRIBING THE PHYSICAL DISTRIBUTION OF AN AGENT IN A PATIENT

FIELD OF THE INVENTION

The present invention relates to the field of surgical pathology, in which a pathologist attempts to convey to a surgeon as rapidly as possible the presence and distribution of cancer in a resected surgical specimen. In particular, the present invention utilizes the biochemical specificity of injectable materials such as radiotracers with digital autoradiography techniques to image the specimen immediately after surgical resection.

BACKGROUND OF THE INVENTION

Current surgical pathology practice consists of having a pathologist receive a surgical specimen immediately after resection. The pathologist marks the specimen with ink to show how the specimen was oriented in the body (i.e., the blue-inked side was facing forward in the body). The pathologist then slices the specimen into thin (i.e., 3 mm thick) slices, and visually inspects the slices. The pathologist then selects the areas that appear visually to have the greatest likelihood of containing cancer, and removes a small section from these pieces. The pathologist freezes these small pieces and shaves thin sections for rapid staining and inspection under a microscope ("frozen section"). The pathologist conveys his or her impression as to the frozen section results to the surgeon, so that the surgeon can decide whether the resection has been adequate. If the frozen section examination suggests that the cancer cells are very close to the margin of the surgical specimen, the surgeon is alerted that the "margins are not clear" and that additional tissue needs to be removed to insure that the entire cancer is gone from the body. Theoretically, the surgeon could have the patient ready on the operating room table for additional removal of tissue pending the pathologists' opinion as to whether this additional removal is needed. In practice, because frozen section examination is fairly inaccurate, most surgeons will not rely on the information from frozen section examination, and will simply complete their surgery and hope that when the final pathological report comes out (several days after surgery) the margins will have been shown to be clear of tumor. The risk of local recurrence of breast cancer is higher if the margins are not clear and if re-excision is not done. As a result, for breast cancer resections, in as many as 30% of cases, a re-excision is needed because the final pathology report comes back saying that the margins were not clear.

The present invention also pertains to the art of autoradiography. Autoradiography is a very old technique for using radiotracers in tissues to form images of radiotracer concentration in the tissues. Autoradiography is typically performed by injecting an animal with a radioactive tracer, sacrificing the animal, and then slicing the animal's organs up and imaging the sliced organs with a detector that is sensitive to radiation emitted by the radioactive tracer. In nearly all cases, the autoradiography detector is sensitive to beta rays emitted by a radioactive tracer. The notable feature of autoradiography is that the specimen is placed in contact with the radiation detector, thereby improving spatial resolution.

The present invention also pertains to the art of radiotracer imaging of human cancers. Radiotracers consists of a chemical compound containing a component that is biologically specific (i.e., binds to a specific type of receptor, cell or organ), and a second component that emits radiation which can be detected by a device placed external to the body. For breast cancer imaging, the most widely used radiotracers are the positron-emitter 2-[F-18] fluorodeoxyglucose (also known as FDG) and the single-photon emitter Tc-99m SestaMIBI (also known as MIBI). FDG can be detected with a positron emission tomography (also known as PET) scanner, or with a special device invented by the applying inventor known as a positron emission mammography scanner. MIBI can be detected with a gamma camera, or with a special device invented by the applying inventor known as a single photon emission mammography scanner. Several investigators have used handheld gamma cameras or non-imaging gamma ray detectors in an operating room to examine the patient's body prior to removal of a cancer, and after removal of a cancer. No investigators have imaged the radioactive cancer after removal from the patient's body in order to assess whether the margins of resection were complete.

The present invention is novel in that it consists of the use of a radiation detector in conjunction with surgically-resected human tumors, in situations where the patient was injected with the cancer-seeking radiotracer prior to surgery. After the human tumor specimen is removed from the patient's body, it is either imaged whole (i.e., without slicing) or is sliced and then the slices imaged with the radiation detector. The radioactive tracer can either be a gamma emitter like Tc-99m labeled SestaMIBI, or it can be a beta emitter like 2-(F-18)Fluorodeoxyglucose.

The present invention is also novel in that it allows comparative imaging of the specimen by x-ray or other methods, and permits simultaneous display of the radiotracer and the x-ray images.

Nobody has imaged a human surgical specimen from a patient injected with radiotracers prior to surgery in order to describe the distribution of tumor in the specimen, and specifically to determine whether a tumor is wholly contained within the surgical specimen. Technically this approach is more easily accomplished than an intraoperative examination for several reasons: First, all the radiation is coming from the specimen when only the specimen is examined, whereas if we were to examine the tumor while it was in the patient we would have to remove the influence of radiation from parts of the body other than the surgical specimen. In the case of breast imaging, this "scatter" from parts of the body other than the breast is much greater than the radiation emitted by the breast, which can make it very challenging to see small tumors well.

SUMMARY OF THE INVENTION

The present invention provides surgeons with information as to the extent and location of cancers or other pathological processes immediately after removal of surgical specimens from the body. This information can help the surgeon decide whether the surgical procedure has been adequate for removal of the patient's tumor, or whether additional tissues must be removed from the patient's body. The current standard of medical care is to employ staining methods that provide such information several days after initial surgery, leading to the need for additional (i.e., re-excision) surgery and anesthesia, which inconveniences the patient and adds to health care costs. By providing early information about the distribution of cancer in the tissue specimen, the invention reassures the patient that initial surgery was most likely curative, and that no additional procedures are needed. Since the invention can rapidly assess whether cancer extends to the margins of the resected specimen, the surgeon can elect to keep the patient on the operating room table while the pathologist inspects the specimen with the invention. If the invention demonstrates that cancer extends to the margins of the specimen, the surgeon can remove more tissue without subjecting the patient to the need for a separate surgical procedure (re-excision). The importance of the invention is illustrated by the fact that at centers of clinical excellence where surgeons perform lumpectomies for breast cancer, as many as a third of lumpectomies require re-excisions.

The present invention comprises an apparatus that is sensitive to a material which is administered to the patient prior to surgery, and which can be detected with the invention after removal of the surgical specimen. The material selectively accumulates in tumor cells, so that images of the surgical specimen with the invention provides information about the presence and distribution of tumor in the surgical specimen. The invention allows comparative anatomic images to be obtained of the surgical specimen so that the surgeon can measure the distance between tumor and the margin of the specimen. In this way the surgeon can assess the likelihood that the specimen margin will be free of tumor.

A primary objective of the present invention is to describe the distribution of cancer or precancerous conditions within a surgical specimen, for a patient who was injected with a substance prior to surgery, which substance concentrates selectively in cancer or precancerous cells (i.e., is tumor-seeking), said system preferably comprising:

a detector sensitive to the substance which is present in the surgical specimen and which selectively concentrates in the cancer or precancer; and an apparatus capable of forming an image based on the information gathered by the detector, and which image describes the physical distribution of the substance in the surgical specimen rapidly so that a surgeon can be guided by the image provided by the apparatus; and a holder capable of compressing the surgical specimen before and/or after slicing of the specimen against the detector so that the spatial resolution of the image is optimized.

A secondary objective of the invention is to compare the distribution of tumor-seeking substance with other descriptive maps, such as x-ray attenuation, said system preferably comprising:

a detector sensitive to the substance which is present in the surgical specimen and which selectively concentrates in the cancer or precancer; and an apparatus capable of forming an image based on the information gathered by the detector, and which image describes the physical distribution of the substance in the surgical specimen rapidly so that a surgeon can be guided by the image provided by the apparatus; and a holder capable of compressing the surgical specimen before and/or after slicing of the specimen against the detector so that the spatial resolution of the image is optimized; and fiduciary markings upon the holder which are visible both on the image of the tumor-seeking agent, as well as on other methods of describing the distribution of tumor or anatomical information; and a computer capable of using the fiduciary marker locations on each image set to register the tumor-seeking image with other image sets and to combine these image sets in order to derive useful information.

The present invention pertains to a system for describing the physical distribution of an agent that accumulates selectively in tissue of a patient in an excised surgical specimen. The system comprises an agent which selectively concentrates in a cancer or precancer or focus of infection or other pathological condition. The system comprises a detector sensitive to the agent which is present in the surgical specimen. The system also comprises an apparatus capable of forming an image based on the information gathered by the detector, and which image describes the physical distribution of the agent in the surgical specimen so that a surgeon can be guided by the image provided by the apparatus, said apparatus connected to said detector.

The present invention pertains to a system for describing the physical distribution of an agent that accumulates selectively in tissue of a patient in an excised surgical specimen. The system comprises an agent which selectively concentrates in a cancer or precancer or focus of infection or other pathological condition. The system comprises a detector sensitive to the agent which is present in the surgical specimen. The system comprises an apparatus capable of forming an image based on the information gathered by the detector, and which image describes the physical distribution of the agent in the surgical specimen so that a surgeon can be guided by the image provided by the apparatus, said apparatus connected to said detector.

BRIEF DESCRIPTION OF THE DRAWINGS

In the accompanying drawings, the preferred embodiment of the invention and preferred methods of practicing the invention are illustrated in which:

FIGS. 1A–1H is a diagram of the preferred embodiment of the invention as it would be employed in a typical patient study.

DESCRIPTION OF THE PREFERRED EMBODIMENT

Figure 2:
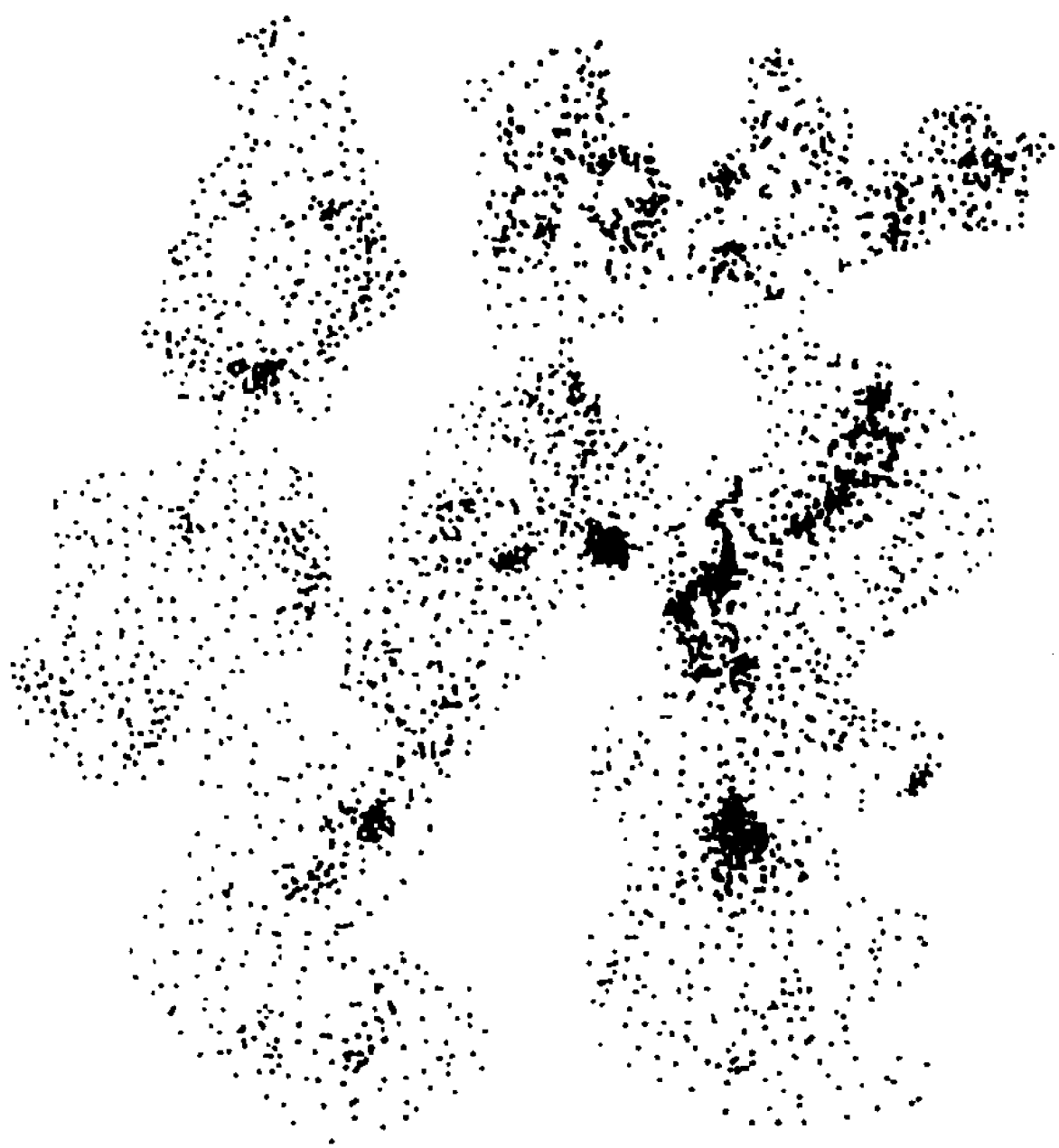
FIG. 2 is an image of the distribution of the radiotracer FDG as obtained in less than 20 minutes with an autoradiography device from a sliced surgical specimen taken from a patient who had been injected with FDG prior to surgery.

Referring now to the drawings wherein like reference numerals refer to similar or identical parts throughout the several views, and more specifically to FIG. 1 thereof, there is shown a system for describing the physical distribution of an agent that accumulates selectively in tissue of a patient in an excised surgical specimen. The system comprises an agent which selectively concentrates in a cancer or precancer or focus of infection or other pathological condition. The system comprises a detector sensitive to the agent which is present in the surgical specimen. The system comprises an apparatus capable of forming an image based on the information gathered by the detector, and which image describes the physical distribution of the agent in the surgical specimen so that a surgeon can be guided by the image provided by the apparatus, said apparatus connected to said detector system as described in Claim 1 including a holder for holding the surgical specimen against the detector so that the resolution of the image is optimized, said holder attached to the detector.

Preferably, the system includes a holder for holding the surgical specimen against the detector so that the resolution of the image is optimized. The holder attached to the detector. Preferably, the agent is a tumor seeking agent. Preferably, the system includes fiduciary markings or other recognizable features for determining the position and orientation of the specimens or specimen holder present upon the holder which are visible on the image of the tumor-seeking agent. Preferably, the system includes a computer which uses the fiduciary marker locations or other recognizable features on each image to register the tumor-seeking image with other images and combines these images to identify the presence and extent of cancer.

Preferably, the tumor-seeking agent is a radiotracer which selectively accumulates in cancers or precancer conditions or focus of infection or other pathological condition, and where the detector is sensitive to radiation from the radiotracer. Preferably, the tumor-seeking agent is a beta-emitting radiotracer which selectively accumulates in cancers or precancer conditions, and where the detector is sensitive to beta rays. Or, the tumor-seeking agent is a gamma-ray emitting radiotracer which selectively accumulates in cancers or precancer conditions, and where the detector is sensitive to gamma rays. Or, the tumor-seeking agent is bromodeoxyuridine that after coupling to another agent can distort electromagnetic fields, and which selectively accumulates in cancers or precancer conditions, and where the detector is sensitive to electromagnetic field perturbations.

Figure 3:
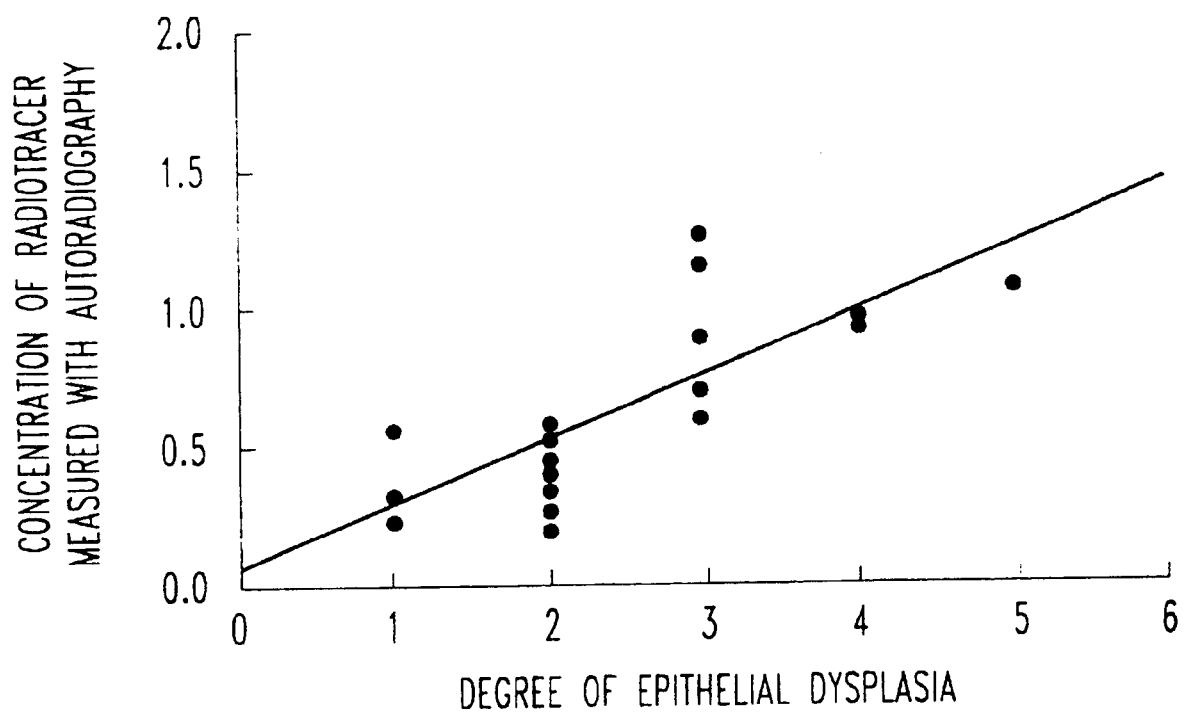
FIG. 3 is a graph showing that the concentration of radiotracer in the radiotracer images correlated with the presence of cancer precursor cells as determined by final pathological examination.
Figure 4:
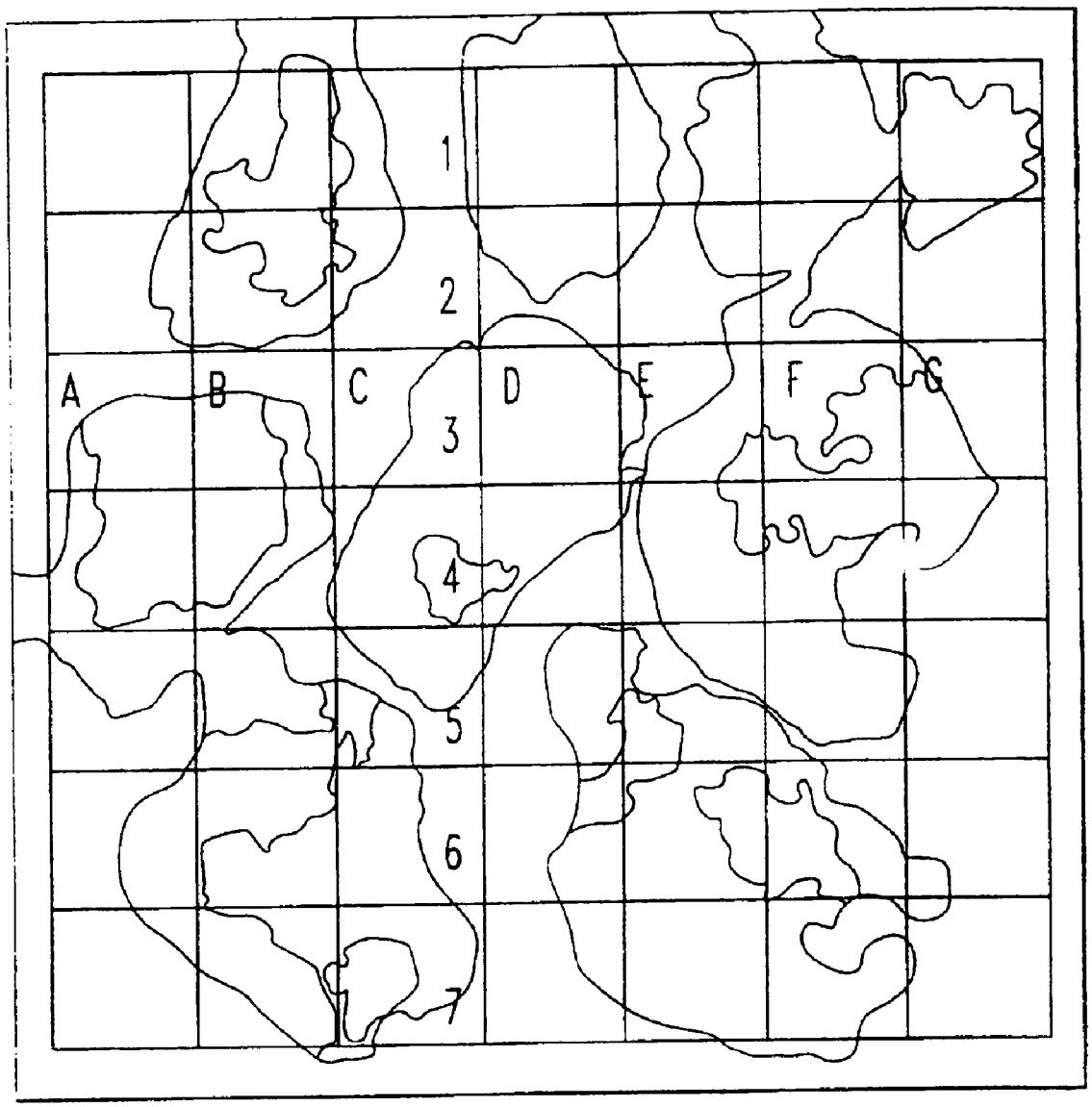
FIG. 4 is an x-ray image of the same sliced surgical specimen showing that the x-ray can be used to provide additional information about the location of abnormal areas of accumulation seen on the radiotracer image.
Figure 5:
FIG. 5 is a processed image in which the radiotracer image has been divided by the x-ray image of the same sliced surgical specimen to render a rough idea of radiotracer concentration per cell of tissue.

The present invention comprises an apparatus sensitive to the presence and distribution of a given material which is present in tissues that have been removed from the body after surgery, and which was administered to the patient (e.g., injected into a patient's vein, as in FIG. 1A) prior to surgery, and which selectively accumulates in malignant cells (FIG. 1B). In one preferred embodiment, the given material is a radioactive substance that concentrates selectively in cells with high metabolic activity, such as the radiotracer 2-[F-18]fluorodeoxyglucose. In this embodiment, the apparatus is sensitive to the beta rays emitted by the F-18. The surgeon removes a piece of tissue containing a cancer, as in FIG. 1C. The surgical specimen is sliced by the pathologist into thin (e.g., 3-mm thick) specimen slices, as is the usual practice today (as in FIG. 1D). Unlike the usual practice of pathologists, which is to shave off sections of the specimen slices for rapid staining and viewing, the user of the introduces the additional step of placing the specimen slices on a gridded tray (as in FIG. 1E). The gridded tray contains fiducial markers that are radio-opaque to x-rays and also emit beta radiation. The pathologist places the detector portion in close proximity (or in contact) to the gridded tray containing the specimen slices (as in FIG. 1F). The beta rays emitted by the slices of tissue are converted into electrical signals by the detector portion, and the electrical signals are received as input data by the computer portion, which processed the input data to form an image corresponding to the distribution of radioactive material in the specimen slices (see FIG. 2). This distribution is related to the location of cancer precursor cells in the specimen slices (see FIG. 3). These results were obtained by having the pathologist analyze small sections of the specimen, and grade the sections on the basis of the degree to which the predominant tissue type in the sample resembled cancer cells (i.e., grade of 1 for fat cells, grade of 2 for normal breast tissue, grade of 3 for sclerosing adenosis, grade of 4 for typical hyperplasia, grade of 4 for atypical hyperplasia, grade of 5 for ductal carcinoma in situ, grade 7 for invasive cancer). In FIG. 3, the abscissa represents the degree of dysplasia assigned for each small section (i.e., each data point represents one small section) by the pathologist. The ordinate represents the quantitative measurement of radiotracer density in the tissue as measured with the beta-sensitive apparatus. After the beta image has been collected, the gridded tray holding the specimens is taken to an x-ray camera which provides a map of x-ray attenuation of the specimen slices (as in FIG. 1G, and FIG. 4). Since the gridded tray has an x-ray opaque grid and also has fiducial markers that are visible both on the beta ray image as well as the x-ray image, the beta ray image can be manipulated through image processing techniques, as is well known in the art, so that the coordinates of any location on the beta ray image are transformed into the coordinate system of the x-ray image (as in FIG. 1H). The beta and x-ray images can then be displayed simultaneously (i.e., whereby the beta image is a color overlay onto the x-ray image). This allows the pathologist to correlate his or her pathological findings with both the beta ray image as well as the x-ray image. It is possible to use the additional information provided by the x-ray image to enhance the utility of the beta ray image. For example, since the beta ray image provides a map of concentration of tumor-seeking radiotracer per unit area, and the x-ray image describes roughly the number of cells per unit area, dividing the beta ray image by the x-ray image gives the map of concentration of tumor-seeking radiotracer per unit cell, which may be a more robust indicator of malignancy than the radiotracer map alone.

In the alternative, there are devices in the market today which are employed by physicians that use different tools to remove (i.e., excise) tissue from the body. This class of tools are called minimally invasive technology. Autoradiographic agents can be injected prior to such procedures involving minimally invasive technology as well as traditional surgery. These devices generally use a tube (i.e., cannula) which cuts through tissue and removes a cylindrical plug.

One such device is the "Abbe" instrument, marketed by U.S. Surgical for biopsy of small breast cancers. This instrument can biopsy a woman's breast while she is reclining on a table, with the breast protruding through a cutout on the table. The Abbe tube removes a plug of tissue which can be sliced just as the surgical specimen is sliced in the patent, and the slices placed within an autoradiographic imager as described herein.

Another device applies suction through the cannula at the time of biopsy. The example of this device is the "Mammotome", marketed by Biopsys, a subsidiary of Johnson and Johnson. The Mammotome removes a "stream" of tissue from the breast. The presence and quantity of the injected agent is monitored in the stream as it is drawn out by the cannula, and also imaged in the specimens that have been removed by the cannula.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

What is claimed is:

1. A method for near real-time determination of the presence and distribution of cancerous, precancerous or abnormal cells in a tissue specimen of a subject comprising the steps of:

administering an agent to the subject, the agent concentrating in the cancerous, precancerous or abnormal cells;

excising a sample of the tissue from the subject;

slicing the sample to prepare sections of the sample;

arranging the sections on a specimen holder;

sealing the specimen holder; and imaging the sections with a receptor sensitive to the agent, the receptor being in close proximity to the sections, to identify the presence and distribution of cancerous, precancerous or abnormal cells within the sections.

2. The method for near real-time determination of the presence and distribution of cancerous, precancerous or abnormal cells in accordance with claim 1 including the steps of providing fiduciary markings on the holder and correlating the imaging with the fiduciary markings.

3. The method for near real-time determination of the presence and distribution of cancerous, precancerous or abnormal cells in accordance with claim 1 wherein the agent is a radiotracer and the receptor is an autoradiography imaging device.

4. The method for near real-time determination of the presence and distribution of cancerous, precancerous or abnormal cells in accordance with claim 3 wherein the radiotracer is a gamma-ray emitting radiotracer.

5. The method for near real-time determination of the presence and distribution of cancerous, precancerous or abnormal cells in accordance with claim 3 wherein the radiotracer is a beta emitting radiotracer.

6. The method for near real-time determination of the presence and distribution of cancerous, precancerous or abnormal cells in accordance with claim 1 including the steps of determining the extent of the presence of cancerous or precancerous cells.

7. The method for near real-time determination of the presence and distribution of cancerous, precancerous or abnormal cells in accordance with claim 1 wherein the agent is capable of distorting an electromagnetic field.

8. The method for near real-time determination of the presence and distribution of cancerous, precancerous or abnormal cells in accordance with claim 1 wherein the agent is capable of attenuating electromagnetic radiation.

9. The method for near real-time determination of the presence and distribution of cancerous, precancerous or abnormal cells in accordance with claim 1 wherein the agent is 2-fluorodeoxyglucose.

10. The method for near real-time determination of the presence and distribution of cancerous, precancerous or abnormal cells in accordance with claim 1 wherein in the arranging step, the specimen is arranged in a 2-dimensional arrangement.

* * * * *